US012178211B2

United States Patent
Lin et al.

(10) Patent No.: US 12,178,211 B2
(45) Date of Patent: Dec. 31, 2024

(54) **ENDOPHYTIC FUNGUS *PSEUDOPHIALOPHORA ORYZAE* P-B313 AND ITS APPLICATION**

(71) Applicant: ZHEJIANG ACADEMY OF AGRICULTURAL SCIENCES, Hangzhou (CN)

(72) Inventors: Fucheng Lin, Hangzhou (CN); Zhenzhu Su, Hangzhou (CN); Lin Li, Hangzhou (CN); Yan Liang, Hangzhou (CN); Kunlun Shen, Hangzhou (CN)

(73) Assignee: ZHEJIANG ACADEMY OF AGRICULTURAL SCIENCES, Hangzhou (CN)

( * ) Notice: Subject to any disclaimer, the term of this patent is extended or adjusted under 35 U.S.C. 154(b) by 200 days.

(21) Appl. No.: 17/744,646

(22) Filed: May 14, 2022

(65) Prior Publication Data

US 2022/0361506 A1    Nov. 17, 2022

(30) Foreign Application Priority Data

May 14, 2021  (CN) .................. 202110529926.X

(51) Int. Cl.
| | | |
|---|---|---|
| *A01N 63/30* | (2020.01) | |
| *A01P 3/00* | (2006.01) | |
| *C12N 1/14* | (2006.01) | |
| *C12R 1/645* | (2006.01) | |

(52) U.S. Cl.
CPC ................ *A01N 63/30* (2020.01); *A01P 3/00* (2021.08); *C12N 1/145* (2021.05); *C12R 2001/645* (2021.05)

(58) Field of Classification Search
CPC ........... A01N 63/30; A01P 3/00; C12N 1/145; C12R 2001/645
See application file for complete search history.

(56) References Cited

FOREIGN PATENT DOCUMENTS

CN            109769535        5/2019

OTHER PUBLICATIONS

Yuan et al (2010, Available Online: Dec. 16, 2009, Applied and Environmental Microbiology, doi:10.1128/AEM.01911-09) {herein Yuan} (Year: 2010).*
Dictionary (2023, https://www.dictionary.com/browse/room-temperature) {herein Dictionary} (Year: 2023).*

* cited by examiner

*Primary Examiner* — Paul J Holland
*Assistant Examiner* — Erica Nicole Jones-Foster
(74) *Attorney, Agent, or Firm* — Jiwen Chen; Joywin IP Law PLLC

(57) ABSTRACT

The present invention discloses an endophytic fungal strain *Pseudophialophora* sp. P-B313 and an application thereof, and belongs to the technical filed of microbial applications. The deposit number of the endophytic fungal strain P-B313 is CCTCC M 2021504, and the scientific name thereof is *Pseudophialophora* sp. The endophytic fungal strain P-B313 can enhance the resistance of rice against seedling leaf blast with a control efficiency of 87.56% and a disease index reduced by 62.59. The biological control efficiency of the endophytic fungus P-B313 against seedling leaf blast in rice has great value by promotion and applications thereof in the field of agriculture.

5 Claims, 3 Drawing Sheets
Specification includes a Sequence Listing.

SEQUENCE LISTING

```
<160> NUMBER OF SEQ ID NOS: 3

<210> SEQ ID NO 1
<211> LENGTH: 558
<212> TYPE: DNA
<213> ORGANISM: Pseudophialophora sp.

<400> SEQUENCE: 1
tgcctgcgga gggatcatta tcgagttgca aaactctaac cctttgtgaa catacctcag      60
tcgttgcttc ggcggtggac ggcctgtttt tcggaacggc cggaagccgc cggaggttcc     120
aaactcgtat tttttagtgt atctctgagc ctgaaaacaa ataatcaaaa ctttcaacaa     180
cggatctctt ggttctggca tcgatgaaga acgcagcgaa atgcgataag taatgtgaat     240
tgcagaattc agtgaatcat cgaatctttg aacgcacatt gcgcccgccg gtattccggc     300
gggcatgcct gttcgagcgt catttcaacc ctcaagccca gcttggtgtt ggggcacccg     360
gccgcctggc cggcccgggg ccctcaagtg tatcggcggt ctcgtcggga ctctgagcgc     420
agtaactcgc ggtaaaacgc gcttcgcttg gtctgtctcc ggcgggctcc ggccgctaaa     480 ccccccctctc tcccagagtt gacctcggat caggtaggat tacccgctga acttaagcat     540
atcaataagc cggaggaa                                                   558

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2
tccgtaggtg aacctgcgg                                                   19

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3
tcctccgctt attgatatgc                                                  20
```

ENDOPHYTIC FUNGUS *PSEUDOPHIALOPHORA ORYZAE* P-B313 AND ITS APPLICATION

This application claims priority to Chinese Patent Application No. 202110529926X filed May 14, 2021, which is hereby incorporated by reference.

FIELD OF TECHNOLOGY

The present invention relates to the technical field of disease control in plants and, in particular, to an endophytic fungal strain *Pseudophialophora* sp. P-B313 and its application in control of seedling leaf blast in rice.

BACKGROUND TECHNOLOGY

Rice blast, also known as rice fever, is an important disease of rice worldwide and is ranked as one of the three major diseases of rice along with sheath blight and bacterial blight. Rice blast is an epidemic transmitted on air currents, posing a great threat to rice production. While the degree of damage varies depending on the cultivars, culture techniques and climatic conditions, a yield reduction of 10%-20% is generally seen, with crop failures in local fields. Rice blast may occur throughout the growth duration of rice. It can be divided into seedling blast, leaf blast, collar blast, node blast, seedling leaf blast, branch blast and grain blast depending on the growth stage and the part of the plant that is affected, among which seedling leaf blast has the greatest impact on yield.

Currently the most cost-effective way for the prevention of the disease is cultivation of a rice cultivar with disease resistance. However, the disease resistance may be lost due to mutation or adaptation of races of the pathogens during long cultivation of a rice cultivar with a single resistance gene, resulting in a recurrence of the disease. Besides, rice blast is generally controlled with chemical fungicides as well. However, prolonged overuse of chemical fungicides not only increases the production cost of rice, but causes safety problems in rice quality and pollution of ecological environment. Therefore, it has become a hot study topic in disease control in plants to search for efficient, environment friendly, green and safe biological control measures.

Biological control is a method of reducing the number of pathogens or the pathogenicity thereof using various adverse effects of beneficial microorganisms on pathogens (such as anti-bacteria effect, bacteriolytic effect, competition, mycoparasitism, etc.); meanwhile, the beneficial microorganisms for biological control may also induce an enhanced disease resistance of plants, enhance the immunity of plants, and delay, relieve or inhibit the induction of diseases.

There are a lot of beneficial microorganisms hiding in the ecological system of the nature, among which are the endophytic fungi in plants. The endophytic fungi in plants refer to a group of fungi which can invade and colonize healthy plant tissues during at least a part of the life cycle thereof without causing apparent disease symptoms in the host. Commonly existing in ecological systems, the endophytic fungi have very stable long-term interactions with the host plants. During the formation of the mutualism between the endophytic fungi in plants and the hosts, on one hand, the endophytic fungi in plants obtain water and mineral nutrients among other nutrients required for growth from the host, while on the other hand, the endophytic fungi in plants also provide the plants with various biological functions, such as promoting the growth of plants, improving the biomass of plants, and enhancing the resistance of host plants against biotic and abiotic stresses.

The invention patent under the application number CN201910044093.0 disclosed a use of an endophytic fungal strain R5-6-1 in control of rice bacterial leaf blight. However, there is no report yet so far of functions of other endophytic fungal strains in wild rice in control of seedling leaf blast in rice.

SUMMARY OF THE INVENTION

An object of the present invention is to provide an endophytic fungal strain from a wild rice, wherein the strain may enhance the resistance of rice against rice blast so as to achieve control of seedling leaf blast in rice.

To achieve the above object, the following technical scheme is adopted herein.

An endophytic fungal strain of *Pseudophialophora* sp. was isolated from the roots of wild rice *Oryza granulate* collected from Yunnan Province. The ITS sequence of the endophytic fungal strain is as set forth in SEQ ID No. 1, and the major biological characteristics thereof are that, the colony grew slowly on a PDA plate and the colony diameter reached 6 cm after the strain grew on the PDA plate at 25° C. for 10 days; aerial mycelia were poorly developed, prostrating on medium surface, and the colony was white; the mycelia were 0.5-4.0 μm in width, with a septum; conidiophores were solitary, unbranched; conidia were elliptic or dumbbell-shaped, 11-15 μm×3.5-6.5 μm, with protrusions at the apex thereof and with a septum, the number of the septum being 0-1. The strain was identified as belonging to *Pseudophialophora* sp., and was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under a deposit number of CCTCC M 2021504, and the scientific name thereof is *Pseudophialophora sp.*

The culture conditions for the endophytic fungus *Pseudophialophora* sp. P-B313 are: inoculation of the mycelia of the endophytic fungus P-B313 on a PDA solid culture medium and incubation at 25° C. in the dark for 5-7 days.

It is demonstrated by the study of the present invention that after colonization of the endophytic fungal strain P-B313 in the root tissues of rice, the control efficiency against seedling leaf blast in rice at seedling stage was up to 87.56%.

Therefore, the present invention provides a use or application of the endophytic fungus *Pseudophialophora* sp. P-B313 in control of rice blast.

The use or application includes: colonization of the endophytic fungus *Pseudophialophora* sp. P-B313 in a root tissue of rice.

Further, the use or application includes: co-cultivation of germinated rice seeds and the endophytic fungus *Pseudophialophora* sp. P-B313 for colonization of the fungus in roots of rice seedlings to enhance resistance of rice against seedling leaf blast at seedling stage.

Preferably, the rice seeds are surface-sterilized and then germinate at 22-25° C. The detailed method is: the rice seeds are peeled, surface-sterilized in 1.0% sodium hypochlorite solution for 15 min and rinsed 3 times using sterile water. The sterilized seeds are then planted in half-strength Murashige and Skoog (MS) medium and cultivated for 2-3 days in a constant-temperature incubator for seed germination.

Preferably, the seeds are planted in half-strength MS medium after radicles emerged from the seeds, and mycelium plugs of the endophytic fungus *Pseudophialophora* sp. P-B313 were inoculated.

Preferably, the conditions of co-cultivation are: cultivation at 22-25° C. for 15-20 days, under light for 16 hours and in the dark for 8 hours per day.

The beneficial effects of the present invention are as follows.

The present invention provides an endophytic fungal strain *Pseudophialophora* sp. P-B313, which can enhance the resistance of rice against rice blast. By co-cultivation of the endophytic fungal strain P-B313 and rice, the fungus colonized the roots of rice seedlings so as to reduce the damage on the leaves caused by the pathogen *Magnaporthe oryzae* and enhance the resistance of rice against seedling leaf blast at seedling stage. The disease index of the control group was 71.48, and the disease index of the strain P-B313 treatment group was 8.89, that is, dropped by 62.59, and the control efficiency reached 87.56%. Popularization and application of the biological control effect of the endophytic fungus P-B313 against seedling leaf blast in rice has great potential in the field of agriculture.

DESCRIPTION OF THE EMBODIMENTS

The present invention is further described hereinafter in combination with detailed embodiments, but the present invention is not limited hereto. Unless otherwise specified, the technical means adopted in the examples are all regular technical means, and the raw materials and reagents are all commercially available.

EXAMPLE 1

Isolation and Identification of Strain *Pseudophialophora* sp. P-B313

I. Isolation and Purification of the Strain P-B313

The strain P-B313 was isolated from the root system of *Oryza granulata* from Yunnan Province. Firstly, the root system of the wide rice was continuously rinsed with tap water and the soil particles and appendages were carefully removed. Healthy root tissues were picked for surface sterilization, and were immersed in 75% ethanol for 1-2 min and 1% sodium hypochlorite for 4-5 min, and subsequently, the roots were rinsed with sterile deionized water three times. The root tissues were cut into 0.5 cm long segments, which were then transferred into 2% malt extract agar (MEA, OXOID; with 50 mg/L of chloramphenicol added to inhibit the growth of endophytic bacteria) plates for incubation at 25° C. in the dark. Endophytic fungal mycelia emerged from the edge of the tissue cuts on the fifth day of culture, and were carefully picked with an inoculation loop and transferred into a fresh PDA medium for purification and cultivation. The strain was recorded as P-B313.

II. Strain Identification

1. Morphological Identification

Figure 1:
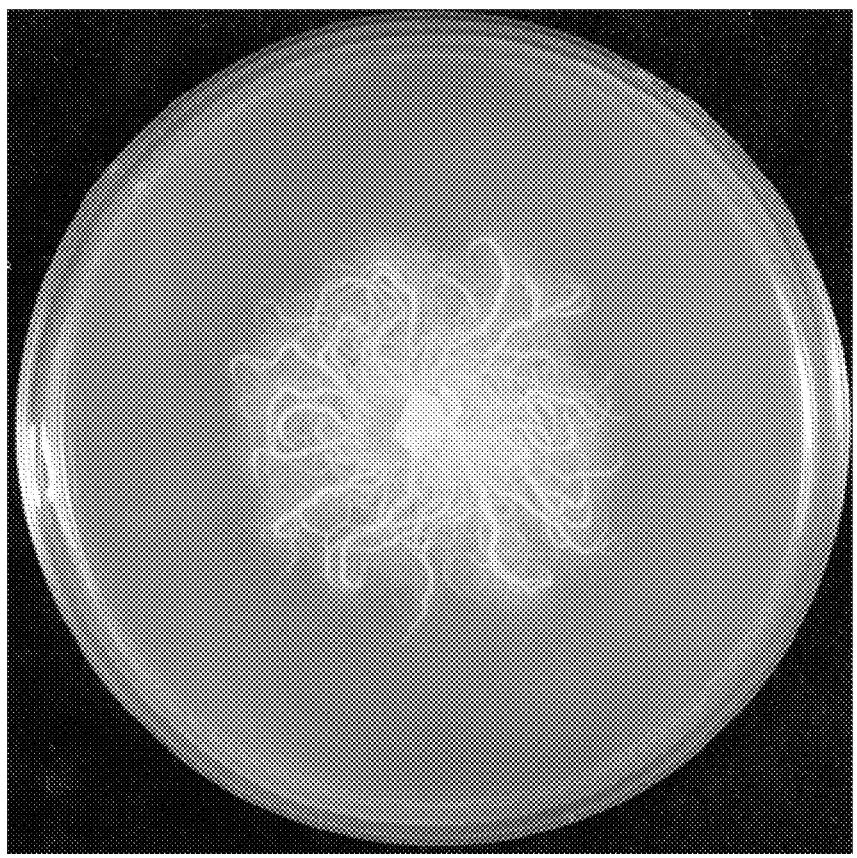
FIG. 1 shows an image of colony morphology of the strain *Pseudophialophora* sp. P-B313.
Figure 2:
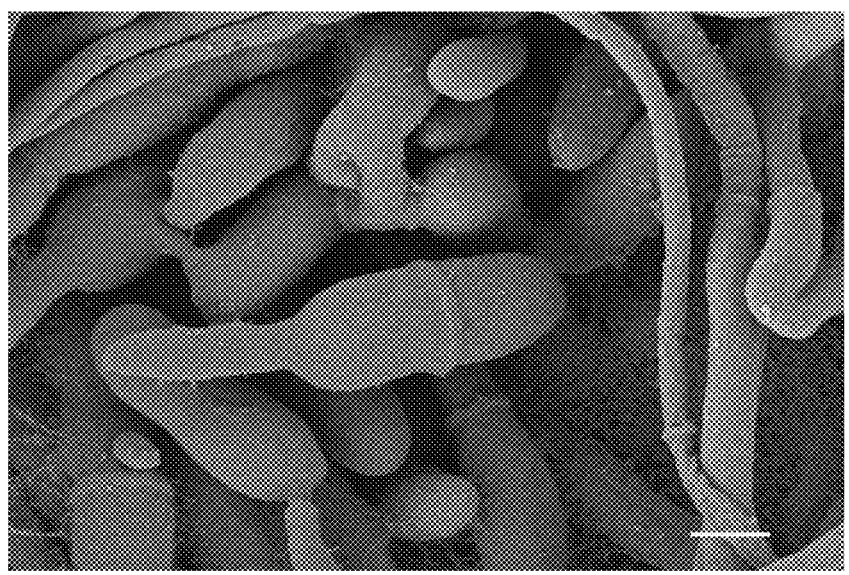
FIG. 2 shows a scanning electron microscope (SEM) image of conidia morphology of the strain *Pseudophialophora* sp. P-B313, where the bar is 2 μm.

The isolated and purified strain P-B313 was inoculated on a PDA medium and cultivated at 25° C. for 7 days. A small amount of the fungal mass was picked with an inoculation loop to prepare a slide for observation, measurement and imaging under an optical microscope. The growth status of the colony is shown in FIG. 1, and the morphology of conidia is shown in FIG. 2.

Figure 3:
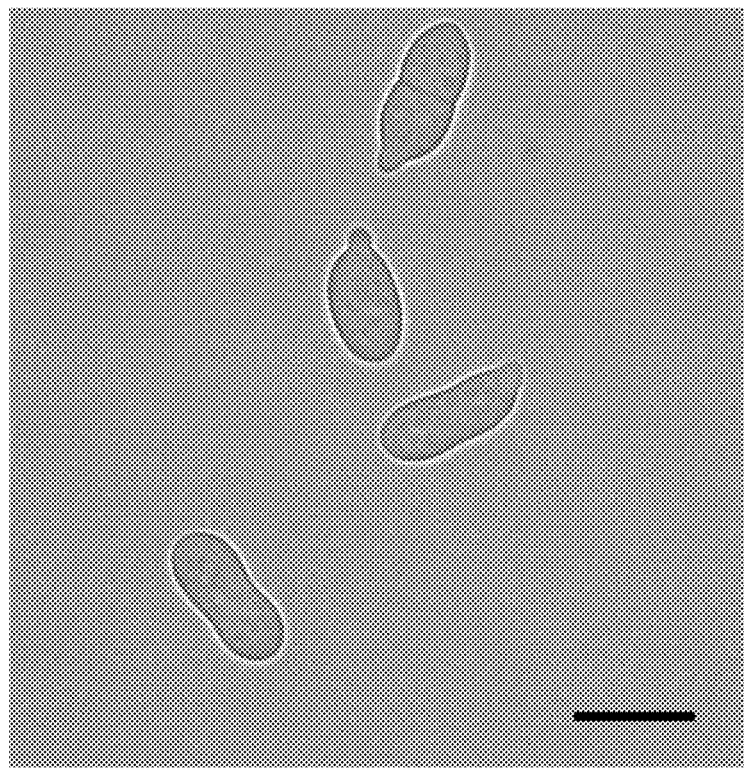
FIG. 3 shows an optical microscope image of conidia morphology of the strain *Pseudophialophora* sp. P-B313, where the bar is 10 μm.
Figure 4:
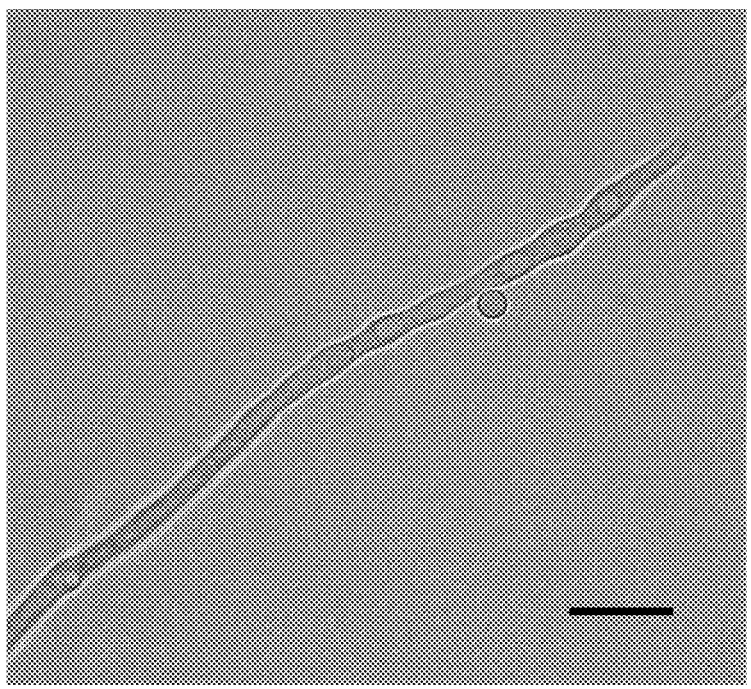
FIG. 4 shows an optical microscope image of mycelia morphology of the strain *Pseudophialophora* sp. P-B313, where the bar is 10 μm.

The morphological characteristics are as follows: the colony grew slowly on the PDA plate, and the colony diameter reached 6 cm after growing at 25° C. for 10 days; the colony was white, the hyphal strands were whorl-like and spiral in shape, and the aerial mycelia were poorly developed. The conidiophores were solitary, unbranched; the conidia were elliptic or dumbbell-shaped, with protrusions (FIG. 3); the mycelia were 0.5-4.0 μm in width (FIG. 4).

2. Molecular Identification (1) DNA Extraction

①After the culture of the strain P-B313 on the PDA plate at 25° C. for 7 days, the mycelia were collected from the plate with a tooth pick and transferred into a sterilized 1.5 mL centrifuge tube containing 300 μL extraction buffer (1 M KCl, 100 mM Tris-HCl, 10 mM EDTA, pH=8.0).

② The fungal mass was pulverized with an electric grinder and vigorously vortexed for 2 min.

③ The mass was centrifuged at 10000 rpm for 10 min.

④ The supernatant was pipetted to a second clean centrifuge tube, and the precipitate was discarded.

⑤ Isopropanol (AR) was added to the supernatant in an equal volume, and mixed by inverting the tube gently several times, then centrifuged at 12000 rpm for 10 min to precipitate the nucleic acid.

⑥ The supernatant was discarded gently, and the centrifuge tube containing the precipitate was put on an absorbent paper upside down to drain water.

⑦ Subsequently, 300 μL 70% ethanol was added and mixed with the precipitate by inverting the tube gently several times and then centrifuged at 12000 rpm for 2 min.

⑧ The supernatant was discarded gently, and step ⑦ was repeated once.

⑨ The centrifuge tube was placed on an absorbent paper upside down to drain water, and placed at 37° C. for 15 min such that ethanol was fully evaporated.

⑩ The precipitate was resuspended in 50 μL ddH$_2$O to obtain the genomic DNA of P-B313 with a concentration up to 30 ng/μL.

(2) PCR Amplification of ITS rDNA Gene of the Fungus

The PCR amplification was performed in a 50 μL reaction system containing: 2 μM each of an upstream primer and a downstream primer, 200 μM of dNTPs, 1.5 mM of MgCl$_2$, 5 μL of 10×PCR buffer, 2 μL of template DNA, and 2 U of Taq enzyme.

The sequence of the upstream primer ITS1 was 5'-TCCGTAGGTGAACCTGCGG-3' (SEQ ID No. 2), and the sequence of the downstream primer ITS4 was 5'-TCCTCCGCTTATTGATATGC-3' (SEQ ID No. 3).

The PCR amplification reaction was carried out with a Longgene MG96G PCR cycler. The PCR cycling conditions consisted of: pre-denaturation at 94° C. for 2 min; then 35 cycles of denaturation at 94° C. for 30 seconds, annealing at 55° C. for 40 seconds and extension at 72° C. for 1 min; and a final extension at 72° C. for 10 min.

(3) Recovery and Purification of PCR Products

After the completion of the PCR reactions, the PCR products were checked by electrophoresis in 1% agarose gel, and then recovered and purified with the DNA gel purification kit of Axygen Biotechnology Limited, following the step-by-step procedure provided in the kit instructions, the steps being as follows.

① All the 50 μL PCR products were loaded in the wells of the 1% agarose gel for electrophoresis and the gel was run at 5 V/CM for 30 min.

② Following the completion of the electrophoresis, a gel slice containing the target DNA fragment was excised with a scalpel blade under ultraviolet illumination, placed in a 2 mL centrifuge tube and weighed.

③ Buffer DE-A was added to the 2 mL centrifuge tube in which the gel was collected based on 3 mL buffer DE-A for each 1 mg gel; the mixture was held at 75° C. for 10 min, during which time it was vortexed several times until the gel was completely melted.

④ Buffer DE-B of 0.5× Buffer DE-A volume was added and mixed well.

⑤ A Miniprep column was placed in the 2 mL centrifuge tube, the mixture was transferred into the Miniprep column, and centrifuged at 12000 rpm for 1 min and the supernatant was discarded.

⑥ The Miniprep column was placed back into the 2 mL centrifuge tube, 500 μL of Buffer W1 was added, and centrifuged at 12000 rpm for 30 seconds.

⑦ The Miniprep column was placed back into the 2 mL centrifuge tube, 700 μL of Buffer W2 was added, and centrifuged at 12000 rpm for 30 seconds.

⑧ Step ⑦ was repeated once.

⑨ The Miniprep column was placed back into the 2 mL centrifuge tube, and centrifuged at 12000 rpm for 2 min to drain the wash buffer on the membrane.

⑩ The Miniprep column was placed back into the 2 mL centrifuge tube, 50 μL ddH$_2$O was added, and centrifuged at 10000 rpm for 1 min. The eluted DNA was stored at −20° C.

(4) Gene Sequencing and Sequence Analysis

The purified and recovered target DNA fragment checked by electrophoresis were delivered to Sangon Biotech (Shanghai) for sequencing with an ABIPRISMA377 automatic sequencer. After strict check of the sequencing result, a DNA fragment sequence as shown in SEQ ID No. 1 with a length of 558 bp was obtained.

Homologous or similar nucleotide sequences were searched for and aligned to the obtained nucleotide sequence by BLAST in the GenBank database on the national center for biotechnology information (NCBI) website. According to the BLAST alignment, the coverage of the sequence and sequences under accession numbers MK808146 and MK808157 was 96% and 95%, respectively, and the identity was 99.44% and 99.25%, respectively. Both of the sequences are ITS rDNAs derived from *Pseudophialophora* sp.

As demonstrated by the above results of molecular identification and morphological identification, the newly isolated strain belongs to *Pseudophialophora* sp. and hence named as *Pseudophialophora* sp. P-B313. The strain was deposited on May 8, 2021 in the China Center for Type Culture Collection (CCTCC) at Wuhan University in Wuhan, China, the recognized IDA under the Budapest Treaty on the International Recognition of the Deposit of Microorganisms for the Purposes of Patent Procedure, under a deposit number of CCTCC M 2021504.

EXAMPLE 2

Test plant: a regular rice cultivar, C039, of *Oryza sativa* L.

1. Culture of Strain P-B313

The strain P-B313 preserved on a filter paper sheet was inoculated on a potato dextrose agar (PDA) solid medium to be activated through culturing at 25° C. for 7 days in the dark, and then set aside.

The PDA medium contained 20 g of dextrose, 200 g of potatoes and 15 g of agar per liter medium. The potatoes were weighed according to the volume of the medium to be prepared, and were boiled, mashed, dissolved and filtered, then added with dextrose and agar, and autoclaved at 121° C. for 20 min.

2. Co-cultivation of Strain P-B313 and Rice Roots

Figure 5:
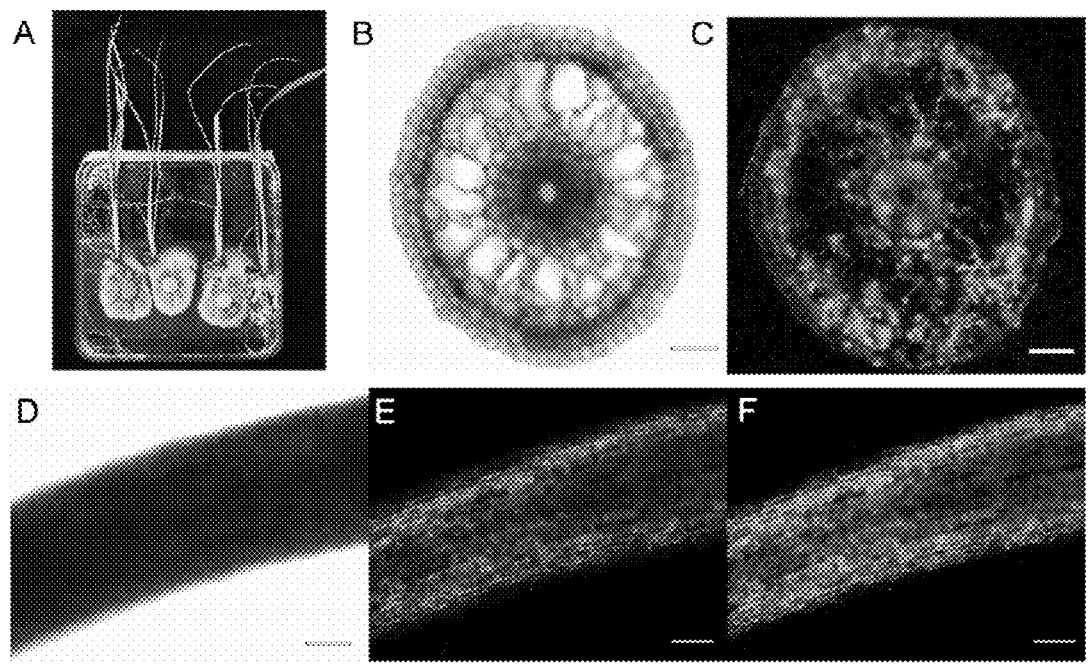
FIG. 5 shows colonization of the strain *Pseudophialophora* sp. P-B313 in rice roots, where the bar is 50 μm. Here, "A" demonstrates the co-cultivation of the strain P-B313 and rice; "B" shows an optical microscope image of a cross-section of a root system inoculated with the strain P-B313; "C" shows a confocal microscope image of a cross-section of a root system inoculated with fluorescent labeled strain P-B313; "D" shows an optical microscope image of a longitudinal section of a root system inoculated with the strain P-B313; "E" shows a confocal microscope image of a longitudinal section of a root system inoculated with fluorescent labeled strain P-B313; and "F" is a combined image of figures "D" and "E".

Rice seeds were peeled and placed in an Erlenmeyer flask, surface-sterilized in 1.0% sodium hypochlorite solution for 15 min, and rinsed 3 times using sterile water and set aside. The sterilized seeds were spread out evenly on a half-strength MS (Murashige and Skoog) medium, sealed with Parafilm sealing film, and placed in a plant incubator set at 25° C. (16 hours under light/8 hours in the dark). When radicles emerged from the seeds in 3 days, the seeds were transferred into tissue culture bottles containing half-strength MS medium, 10 seeds per bottle. Three mycelium plugs (diameter 0.5 cm) of P-B313 were inoculated. Blank PDA agar blocks were used as control. 3 replications were carried out. When rice seedlings grew to the stage of 3 leaves on main shoot and fourth appearing (15-20 days), colonization of the endophytic fungus in roots was observed (FIG. 5), and leaves were used for inoculation with the pathogen *Magnaporthe oryzae*.

3. Spray of Conidia of Pathogen *Magnaporthe oryzae*

The pathogen *Magnaporthe oryzae* Guy11 was inoculated in a CM solid medium and cultured at 25° C. under light for 10-12 days. The conidia of Guy11 were collected by rinsing the medium with sterile water, then filtered through 3 layers of filter paper and prepared into a spore suspension with a concentration of $1\times10^5$. Then a 0.4% gelatin solution was prepared and mixed with the spore suspension according to a 1:1 volume ratio such that the final concentration of the spore suspension of *Magnaporthe oryzae* was $5\times10^4$.

The CM medium (1 L) contained: Yeast Extract (1 g), Casamino acid (1 g), D-glucose (10 g), KH$_2$PO$_4$ (1.52 g), NaNO$_3$ (6 g), Peptone140 (2 g), KCl (0.52 g), MgSO$_4$·7H$_2$O (0.52 g), 0.1% (v/v) Vitamin solution, and 0.1% (v/v) Trace Element. The pH was adjusted to 6.5 with NaOH, and 15 g/L agar was added to the solid medium. The medium was autoclaved at 121° C. for 15 min for sterilization.

The leaves of rice seedlings were sprayed evenly with the spore suspension using a sprayer, 1 mL suspension per bottle. Then the tissue culture bottles were placed in a plant incubator and incubated at 25° C. in the dark for 2 days. After 2 days, light was supplemented (light 16 hours/darkness 8 hours) for a further cultivation of 4-5 days. The scales of rice leaf blast were recorded and the disease index were calculated.

Figure 6:
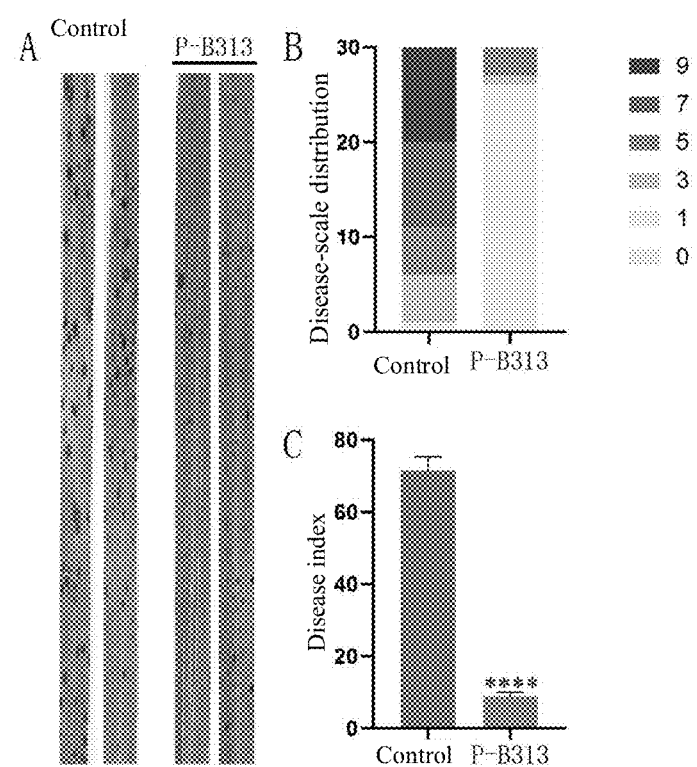
FIG. 6 shows control efficiency of the strain *Pseudophialophora* sp. P-B313 on seedling leaf blast in rice, where "A" demonstrates the disease severity of rice blast on leaves in the strain P-B313 treatment group and the control group; "B" shows a disease-scale index frequency distribution of seedling leaf blast in the strain P-B313 treatment group and the control group; and "C" demonstrates the disease index of seedling leaf blast in the strain P-B313 treatment group and the control group, the data in the charts being mean±SD. Significance level (t-test): ****$P<0.0001$.

The results are shown in FIG. 6. In the control groups, the seedling leaf blast was serious, and the disease scale on leaves fell mainly between 7-9, and the disease index was 71.48. In the strain P-B313 treatment group, the incidence of seedling leaf blast was significantly reduced, with the disease scales on most leaves fell between 0-1, and the disease index was 8.89, and compared with the control group, the disease index decreased by 62.59, and the control efficiency reached 87.56%.

The invention claimed is:

1. A method of controlling of rice blast by utilizing an endophytic fungus *Pseudophialophora* sp. P-B313, comprising the following steps:
   surface-sterilizing rice seeds;
   germinating the rice seeds at 22-25° C.;
   co-cultivating germinated rice seeds and the endophytic fungus *Pseudophialophora* sp. P-B313 for colonization of the fungus in roots of rice seedlings to enhance resistance of rice against seedling leaf blast at seedling stage;
   wherein the deposit number for the endophytic fungus *Pseudophialophora* sp. P-B313 is CCTCC M 2021504 and the scientific name thereof is *Pseudophialophora* sp.

2. The method of claim 1, wherein the seeds are transferred into a half-strength Murashige and Skoog (MS) medium after radicles emerge from the seeds, and mycelium plugs of the endophytic fungus *Pseudophialophora* sp. P-B313 are inoculated.

3. The method of claim 1, wherein conditions of co-cultivation are: cultivation at 22-25° C. for 15-20 days, under light for 16 hours and in the dark for 8 hours per day.

4. The method according to claim 1, wherein the internal transcribed spacer (ITS) sequence of the strain is as set forth in SEQ ID No. 1.

5. The method according to claim 1, wherein a colony diameter reaches 6 cm after the strain grows on a potato dextrose agar (PDA) medium plate at 25° C. for 10 days; aerial mycelia are poorly developed, prostrating on a surface of the PDA medium, and a colony is white; the mycelia are 0.5-4.0 μm in width, with a septum; conidiophores are solitary, unbranched; conidia are elliptic or dumbbell-shaped, 11-15 μm×3.5-6.5 μm in size, with protrusions at an apex thereof and with a septum, a number of the septum being 0-1.

* * * * *